United States Patent [19]

Osawa et al.

[11] Patent Number: 5,128,472

[45] Date of Patent: Jul. 7, 1992

[54] 2,5-DISUBSTITUTED PYRAZINE DERIVATIVES, PYRIMIDINE DERIVATIVES, AND LIQUID CRYSTAL CONTAINING THE SAME

[75] Inventors: Masashi Osawa; Tadao Shoji; Sadao Takehara; Hiroshi Ogawa, all of Chiba; Toru Fujisawa, Saitama; Takeshi Kuriyama; Kayoko Nakamura, both of Chiba, all of Japan

[73] Assignees: Dainippon Ink and Chemicals, Inc., Tokyo; Kawamura Institute of Chemical Research, Sakura, both of Japan

[21] Appl. No.: 606,662

[22] Filed: Oct. 31, 1990

Related U.S. Application Data

[62] Division of Ser. No. 325,813, Mar. 20, 1989, Pat. No. 4,997,942.

[30] Foreign Application Priority Data

Apr. 25, 1988 [JP] Japan ................... 63-100255
Jun. 20, 1988 [JP] Japan ................... 63-150230
Feb. 2, 1989 [JP] Japan ................... 1-24265

[51] Int. Cl.$^5$ .................... C07D 239/02; C09K 19/34
[52] U.S. Cl. ................... 544/335; 252/299.61
[58] Field of Search .............. 252/299.01, 299.61, 252/299.5; 350/355; 544/242, 303, 305, 335

[56] References Cited

U.S. PATENT DOCUMENTS

| | | | |
|---|---|---|---|
| 4,765,924 | 8/1988 | Inoue et al. | 252/299.61 |
| 4,808,333 | 2/1989 | Huynh-ba et al. | 252/299.66 |
| 4,812,258 | 3/1989 | Krause et al. | 252/299.61 |
| 4,818,430 | 4/1989 | Saito et al. | 252/299.61 |
| 4,820,839 | 4/1989 | Krause et al. | 544/316 |
| 4,834,904 | 5/1989 | Krause et al. | 252/299.01 |

FOREIGN PATENT DOCUMENTS

| | | |
|---|---|---|
| 0084194 | 7/1983 | European Pat. Off. |
| 225195 | 6/1987 | European Pat. Off. |
| 0260910 | 3/1988 | European Pat. Off. |
| 3315295 | 10/1984 | Fed. Rep. of Germany |
| 3600052 | 7/1987 | Fed. Rep. of Germany |
| 8606401 | 11/1986 | Israel |
| 60-92276 | 5/1985 | Japan |
| 62-22889 | 1/1987 | Japan |
| 63-253075 | 10/1988 | Japan |

OTHER PUBLICATIONS

Chemical Abstracts, vol. 111, No. 16, Oct. 16, 1989, p. 678, abstract No. 144259z, Columbus, Ohio, U.S.; JP-A-01 79 160 (Dainippon Ink and Chemicals, Inc.) Mar. 24, 1989.

*Primary Examiner*—Robert L. Stoll
*Assistant Examiner*—Shean C. Wu
*Attorney, Agent, or Firm*—Armstrong, Nikaido, Marmelstein, Kubovcik & Murray

[57] ABSTRACT

A 2,5-disubstituted pyrizine derivative and a 2,5-disubstituted pyrimidine derivative of the formula (I):

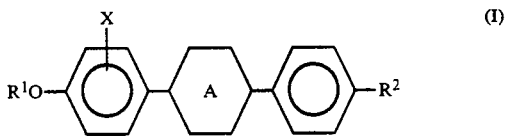

(I)

wherein $R^1$ and $R^2$ each independently represents a straight-chain or branched alkyl group containing 1 to 20 carbon atoms;
X represents a halogen atom; and

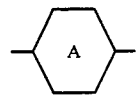

represents a pyrazine-2,5-diyl or a pyrimidine-2,5-diyl group;

each useful as an electrooptical display material are disclosed. Further a liquid crystal composition comprising said compounds as well as a ferroelectric display device wherein said liquid crystal composition is used are disclosed.

5 Claims, No Drawings

2,5-DISUBSTITUTED PYRAZINE DERIVATIVES, PYRIMIDINE DERIVATIVES, AND LIQUID CRYSTAL CONTAINING THE SAME

This is a division of application Ser. No. 325,813 filed Mar. 20, 1989, now U.S. Pat. No. 4,997,942.

FIELD OF THE INVENTION

This invention relates to a 2,5-disubstituted pyrazine derivative, a 2,5-disubstituted pyrimidine derivative, each useful as an electrooptical display material, a liquid crystal composition comprising the same and a ferroelectric liquid crystal display device wherein said composition is used.

BACKGROUND OF THE INVENTION

Recently, liquid crystal display cells excellent in high-speed response, wherein ferroelectric liquid crystals proposed by N. A. Clark et al. are used, have been applied to large-sized liquid crystal displays. The light switching of a chiral smectic C phase (which will be called an "$S_C*$ phase" hereinafter) is applied to these display cells. A chiral smectic liquid crystal mixture obtained by adding a chiral compound to a liquid crystal mixture showing a smectic C phase (which will be called an "$S_C$ phase" hereinafter) is effective as the above-mentioned liquid crystal material showing an $S_C*$ phase.

In order to secure a wide operating temperature range of a display cell of the above-mentioned type, it is required that the chiral smectic liquid crystal mixture shows the $S_C*$ phase over a wide range of temperature.

In the preparation of the chiral smectic C liquid crystal mixture showing an $S_C*$ phase over a wide range of temperature, it is effective to use a smectic C liquid crystal mixture, to which a chiral compound is to be added, showing an $S_C$ phase over a wide range of temperature.

A common method for the preparation of a smectic liquid crystal mixture showing an $S_C$ phase over a wide range of temperature comprises mixing smectic liquid crystals showing an $S_C$ phase within a low temperature range with those showing an $S_C$ phase within a high temperature range. Thus there has been desired to provide various smectic liquid crystal compounds satisfying the following three requirements.

(1) It shows an $S_C$ phase over a wide range of temperature.

(2) It shows no higher-order smectic phase than that of the $S_C$ phase.

(3) It lowers the melting point, when mixed with a smectic liquid crystal mixture showing an $S_C$ phase.

It has been further desired to provide various smectic liquid crystal compounds which can enlarge the $S_C$ phase temperature range of the resulting composition, when added to a smectic liquid crystal mixture showing an $S_C$ phase.

SUMMARY OF THE INVENTION

It is an object of the present invention to provide a novel liquid crystal compound showing an $S_C$ phase or to provide a novel compound which enlarges the $S_C$ phase temperature range of the resulting composition, when mixed with a smectic liquid crystal mixture showing an $S_C$ phase.

In order to achieve the above object, the present invention provides a compound of the following general formula (I):

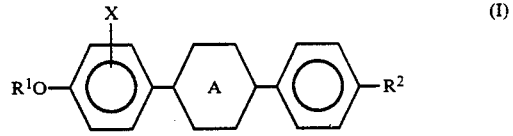

wherein $R^1$ and $R^2$ each independently represents a straight chain or branched alkyl group containing 1 to 20 carbon atoms;

X represents a halogen atom; and

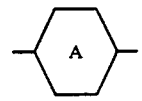

represents a pyrazine-2,5-diyl or a pyrimidine-2,5-diyl group.

DETAILED DESCRIPTION OF THE INVENTION

The compound of the general formula (I) of the present invention may be prepared by the following methods.

(1) When

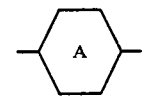

is a pyrazine-2,5-diyl group:

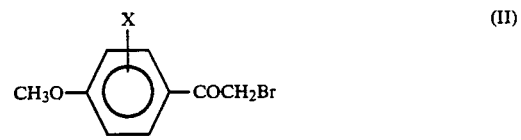

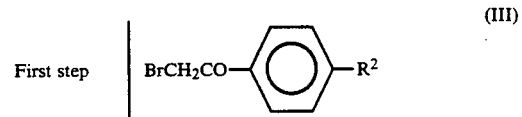

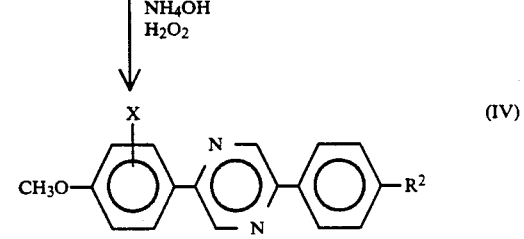

-continued

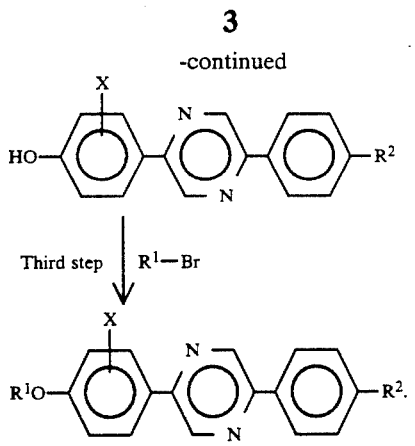

In the above formulae (11), (111), (IV) and V), $R^1$, $R^2$ and X are the same as defined in the formula (I).

First step: Equimolar amounts of the compounds (II) and (III) are reacted with conc. aqueous ammonia in an alcohol solvent such as ethanol, methanol or cellosolve at 50° to 70° C. for ten hours and subsequently with an aqueous solution of hydrogen peroxide at room temperature for ten hours. Then the compound (IV) is separated from the obtained crude reaction product by silica gel column chromatography Second step: The compound (IV) is heated under reflux in acetic acid together with hydrobromic acid for five to ten hours to thereby give the compound (V).

Third step: The compound (V) is reacted with an alkyl bromide in a solvent mixture of dimethyl sulfoxide and tetrahydrofuran in the presence of potassium-tert-butoxide to thereby give the compound (I-a) of the present invention.

(2) When

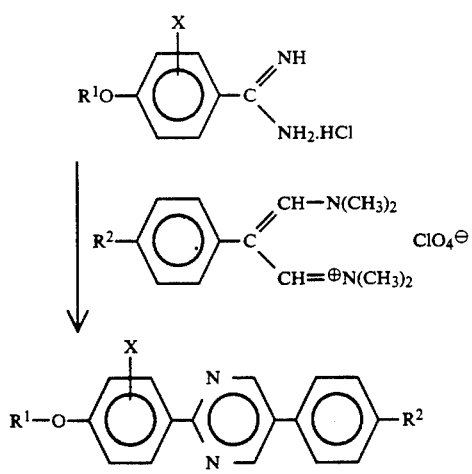

is a pyrimidin 2,5-diyl group:

In the above formulae (VI) and (VII), $R^1$, $R^2$ and X are the same as defined in the general formula (I).

The halogen substituted 4-alkoxyphenylamidine hydrochloride of the formula (VI) is reacted with the 3-dimethylamino-2-(4-alkylphenyl)-2-propene-N,N-dimethyl iminium perchlorate of the formula (VII) in an absolute alcohol in the presence of a basic material such as an alcoholate at the refluxing temperature. The obtained reaction mixture is cooled to room temperature and then water is added thereto. The crystals thus precipitated are filtered, washed with water and vacuum-dried. The crude crystals thus obtained are purified by silica gel column chromatography and further recrystallized from ethanol to thereby give the compound (I-b) of the present invention.

The halogen substituted 4-alkoxyphenylamidine hydrochloride of the formula (VI) may be prepared by, for example, the following method.

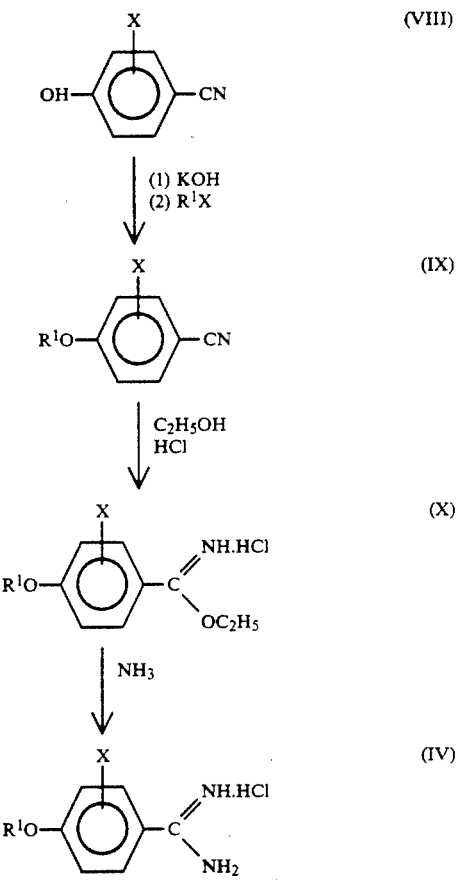

Namely, a halogen substituted 4-cyanophenol is converted into an alcoholate with the use of an alkali such as potassium hydroxide. The alcoholate is then reacted with an alkyl halide to thereby give a halogen substituted 4-alkoxyphenylbenzonitrile which is then reacted with ethanol and hydrochloric acid to thereby give an imino ester hydrochloride. Subsequently the product is reacted with ammonia. Thus the aimed halogen substituted 4-alkoxyphenylacetamidine hydrochloride of the formula (VI) is obtained.

The 3-dimethylamino-2-(4-alkylphenyl)-2-propene-N,N-dimethyliminium perchlorate of the formula (VII) may be prepared by, for example, the following method.

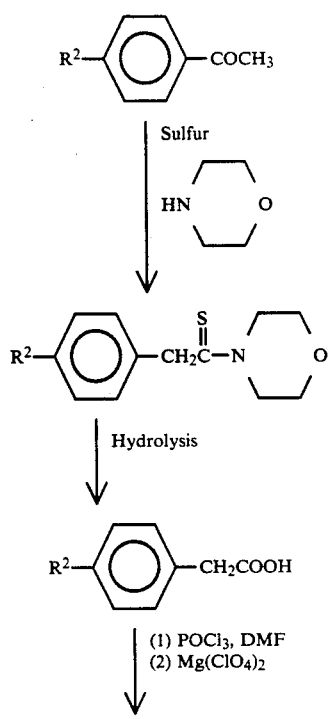

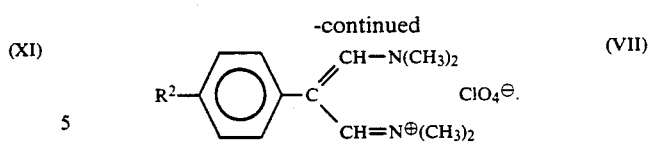

Namely, a 4-alkylacetophenone is reacted with sulfur and morpholine to thereby synthesize a 4-[2-(4-alkylphenyl)-1-thioxoethyl]morpholine which is then hydrolyzed to thereby give 4-alkylphenylacetic acid. The 4-alkylphenylacetic acid thus obtained is reacted with a Vilsmeier reagent, obtained from phosphorus oxychloride and dimethylformamide, and treated with perchlorate. Thus the 3-dimethylamino-2-(4-alkylphenyl)-2-propene-N,N-dimethyliminium perchlorate is obtained.

Table 1 summarizes the phase transition temperatures of typical examples of the compound (I) thus obtained.

The liquid crystal phases and phase transition temperatures of each compound are determined with a polarization microscope provided with a temperature control stage and a differential scanning calorimeter (DSC). However the phase transition temperature would somewhat vary depending on the purity of a sample or the determination conditions.

TABLE 1-1

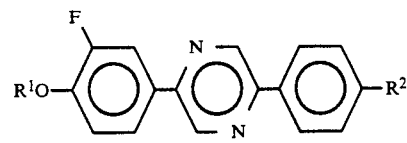

| Compound No. | $R^1$ | $R^2$ | C | $S_C$ | $S_A$ | N | I |
|---|---|---|---|---|---|---|---|
| 1 | $CH_3-$ | $-n-C_6H_{13}$ | °138.3 | °143.5 | °167.1 | °184.4 | ° |
| 2 | $C_2H_5-$ | $-n-C_6H_{13}$ | °117.1 | °174.2 | °183.0 | °194.2 | ° |
| 3 | $n-C_3H_7-$ | $-n-C_6H_{13}$ | °119.7 | °173.9 | °181.8 | °185.6 | ° |
| 4 | $n-C_4H_9-$ | $-n-C_6H_{13}$ | °106.2 | °180.9 | °185.5 | °187.4 | ° |
| 5 | $n-C_5H_{11}-$ | $-n-C_6H_{13}$ | °101.6 | °177.2 | °181.3 | — | ° |
| 6 | $n-C_6H_{13}-$ | $-n-C_6H_{13}$ | °95.6 | °178.2 | °180.1 | °181.1 | ° |
| 7 | $n-C_7H_{15}-$ | $-n-C_6H_{13}$ | °93.8 | °175.3 | °176.6 | — | ° |
| 8 | $n-C_9H_{19}-$ | $-n-C_6H_{13}$ | °93.0 | °170.5 | °172.2 | — | ° |
| 9 | $CH_3-$ | $-n-C_9H_{19}$ | °133.3 | — | °163.7 | °173.7 | ° |
| 10 | $C_2H_5-$ | $-n-C_9H_{19}$ | °107.8 | °159.2 | °181.0 | °184.2 | ° |
| 11 | $n-C_3H_7-$ | $-n-C_9H_{19}$ | °103.2 | °163.4 | °179.4 | — | ° |
| 12 | $n-C_4H_9-$ | $-n-C_9H_{19}$ | °90.2 | °172.6 | °182.7 | °182.8 | ° |
| 13 | $n-C_5H_{11}-$ | $-n-C_9H_{19}$ | °92.7 | °174.9 | °178.5 | — | ° |
| 14 | $n-C_6H_{13}-$ | $-n-C_9H_{19}$ | °86.6 | °175.4 | °176.7 | — | ° |
| 15 | $n-C_7H_{15}-$ | $-n-C_9H_{19}$ | °92.0 | °175.0 | — | — | ° |
| 16 | $n-C_8H_{17}-$ | $-n-C_9H_{19}$ | °92.2 | °174.1 | — | — | ° |
| 17 | $n-C_9H_{19}-$ | $-n-C_9H_{19}$ | °94.5 | °171.7 | — | — | ° |
| 18 | $\begin{array}{c}CH_3\\|\\C_2H_5CHCH_2-\end{array}$ | $-n-C_9H_{19}$ | °91.2 | °148.2 | °151.9 | — | ° |
| 19 | $CH_3-$ | $-n-C_7H_{15}$ | °134.5 | — | °165.7 | °182.0 | ° |
| 20 | $\begin{array}{c}CH_3\\|\\C_2H_5CH(CH_2)_3\end{array}$ | $-n-C_7H_{15}$ | °85.0 | °165.0 | — | — | ° |

TABLE 1-2

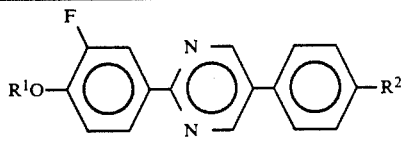

| Compound No. | R¹ | R² | C | $S_c$ | $S_A$ | I |
|---|---|---|---|---|---|---|
| 21 | $CH_3-$ | $-n-C_7H_{15}$ | °70.0 | — | °176.5 | ° |
| 22 | $n-C_6H_{13}$ | $-n-C_7H_{15}$ | °80.5 | °143.5 | °181.0 | ° |
| 23 | $n-C_7H_{15}$ | $-n-C_7H_{15}$ | °82.0 | °140.5 | °178.0 | ° |
| 24 | $n-C_8H_{17}$ | $-n-C_7H_{15}$ | °72.0 | °134.5 | °175.5 | ° |
| 25 | $CH_3\!-\!(CH_2)_{\overline{2}}CH\!-\!(CH_2)_{\overline{3}}$ with $CH_3$ branch | $-n-C_7H_{15}$ | °69.5 | °138.5 | °160.5 | ° |

TABLE 1-3

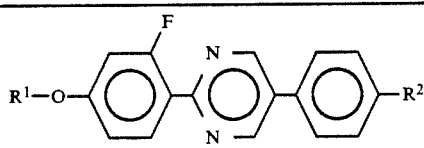

| Compound No. | R¹ | R² | C | $S_c$ | N | I |
|---|---|---|---|---|---|---|
| 26 | $n-C_8H_{17}-$ | $-n-C_8H_{17}$ | °75.0 | °133.0 | °150.0 | ° |
| 27 | $n-C_8H_{17}-$ | $-n-C_5H_{11}$ | °80.0 | °98.5 | °161.5 | ° |
| 28 | $n-C_8H_{17}-$ | $-n-C_6H_{13}$ | °77.5 | °116.0 | °154.0 | ° |
| 29 | $n-C_8H_{17}-$ | $-n-C_7H_{15}$ | °78.5 | °131.0 | °156.0 | ° |

TABLE 1-4

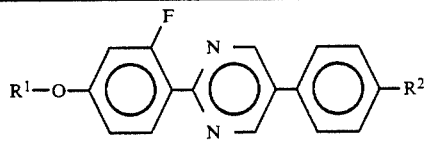

| No. | R¹ | R² | C | $S_c$ | $S_A$ | N | I |
|---|---|---|---|---|---|---|---|
| 30 | $CH_3$ branch on $C_2H_5-CH-(CH_2)_{\overline{3}}$ | $-n-C_8H_{17}$ | °94 | °108 | — | °114.5 | ° |
| 31 | $CH_3$ branch on $n-C_3H_7-CH-(CH_2)_{\overline{3}}$ | $-n-C_8H_{17}$ | °81 | °112 | — | °136.5 | ° |
| 32 | $CH_3$ branch on $C_2H_5-CH-(CH_2)_{\overline{7}}$ | $-n-C_8H_{17}$ | °63 | °118 | — | °143 | ° |
| 33 | $CH_3$ branch on $CH_3-CH-(CH_2)_{\overline{7}}$ | $-n-C_8H_{17}$ | °59 | °105.5 | — | °138.5 | ° |
| 34 | $CH_3$ branch on $n-C_3H_7-CH-(CH_2)_{\overline{5}}$ | $-n-C_8H_{17}$ | °58 | °118.5 | — | °139 | ° |
| 35 | $CH_3$ branch on $C_2H_5-CH-CH_2-$ | $-n-C_7H_{15}$ | °90 | °112.5 | °121 | °130 | ° |

In the above Table 1, C represents a crystal phase; $S_C$ represents a smectic C phase, $S_A$ represents a smectic A phase; N represents a nematic phase; I represents an isotropic liquid phase; ° represents the presence of the corresponding phase; and - represents the absence of the same.

Most pyrazine derivatives, in particular, such 2,5-disubstituted pyrazines as the one of the formula (I) according to the present invention, wherein three rings are bound to each other via no binding group and the pyrazine ring is located at the center, have each a symmetric structure where the substituent at the 2-position of the pyrazine ring is the same as that at the 5-position of the same (cf. H. Schubert et al., J. Prakt. Chem. (4), 37, 12 (1968)). Although JP-A-58-43961 (the term "JP-A" as used herein means an "unexamined published Japanese Patent Application") discloses pyrazine derivatives wherein the substituent at the 2-position of the pyrazine ring is different from that at the 5-position of the same, it describes nothing about the liquid crystal phase of these compounds. In addition, most of these derivatives have high melting points.

The compounds of the formula (I) of the present invention generally show a wide range of the $S_C$ phase temperature of about 50° to 70° C., though it varies depending on the chain-lengths of the alkyl groups. Even the compound No. 1, wherein R is a methyl group, shows an $S_C$ phase (cf. Table 1), which indicates that the compounds of the formula (I) of the present invention are highly useful from the viewpoint of the viscosity of the liquid crystals.

It is generally believed that the viscosity of a liquid crystal compound would decrease with a decrease in the alkyl chain length thereof (cf. S. Matsumoto, "Ekisho Electronics", P. 49, OHM Co. JAPAN (1986)). Each compound of the formula (I) of the present invention shows an $S_C$ phase even when the alkyl groups are short chain ones, such as methyl or ethyl groups. Therefore it may be understood that the compounds of the formula (I) of the present invention are highly useful as a material for preparing a smectic liquid crystal mixture showing an $S_C$ phase.

Furthermore Table 1 obviously indicates that each compound of the formula (I) of the present invention shows no higher-order smectic phase than that of the $S_C$ phase. This fact suggests that no higher-order smectic phase would appear in the preparation of a smectic liquid crystal mixture showing an $S_C$ phase.

Table 1 further indicates that the compounds of the present invention wherein both of the $R^1$ and $R^2$ groups have sufficient numbers of carbon atoms and either $R^1$ or $R^2$ groups is a branched alkyl group, such as the compounds No. 32, No. 33 and No. 34, show each a larger decrease in the melting point than those wherein both of the $R^1$ and $R^2$ groups are straight-chain alkyl groups such as the compound No. 26 does. Although the compounds No. 30 and No. 31 show each rather an increase in the melting point, these compounds would cause a larger decrease in the melting point when formulated into a mixture, than the compound No. 26 does.

These facts are obviously shown by the following Table 2 which shows the phase transition temperatures of compositions obtained by adding 15% by weight of the compound No. 26, No. 30, No. 31 or No. 32 to $S_C$ maternal liquid crystals (A) comprising a bicyclic pyrimidine derivative.

TABLE 2

| Compound No. | Phase Transition Temperatures (°C.) |
|---|---|
| None | C $\xrightarrow{14}$ $S_C$ $\xrightleftharpoons{57}$ $S_A$ $\xrightleftharpoons{64.5}$ N $\xrightleftharpoons{69}$ I |
| 26 | C $\xrightarrow{10}$ $S_C$ $\xrightleftharpoons{67}$ $S_a$ $\xrightleftharpoons{71}$ N $\xrightleftharpoons{79}$ I |
| 30 | C $\xrightarrow{8}$ $S_C$ $\xrightleftharpoons{64}$ $S_A$ $\xrightleftharpoons{70.5}$ N $\xrightleftharpoons{78}$ I |
| 31 | C $\xrightarrow{6}$ $S_C$ $\xrightleftharpoons{63.5}$ $S_A$ $\xrightleftharpoons{70.5}$ N $\xrightleftharpoons{76.5}$ I |
| 32 | C $\xrightarrow{5}$ $S_C$ $\xrightleftharpoons{63}$ $S_A$ $\xrightleftharpoons{70}$ N $\xrightleftharpoons{78}$ I |

The maternal liquid crystals (A) comprises 35% by weight of

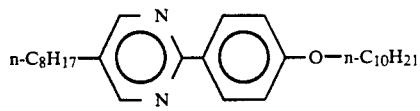

35% by weight of

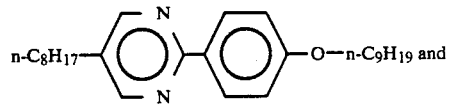

30% by weight of

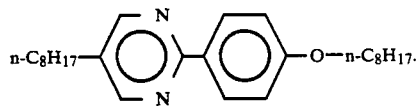

As described above, it can be understood that a compound of the formula (I) having a branched alkyl group would effectively lower the melting point of the $S_C$ maternal liquid crystals and enlarge the $S_C$ phase temperature range to a lower region, as compared with those containing straight-chain alkyl groups.

To further illustrate the present invention, and not by way of limitation, the following Examples will be given. In the Example, parts and percents are by weight unless otherwise specified.

EXAMPLE 1

Preparation of 2-(3-fluoro-4-methoxyphenyl) 5-(4-n-hexylphenyl)pyrazine (compound No. 1 in Table 1)

24.7 g of 2-fluoro-4-(1-oxo-2-bromoethyl)anisole and 28.3 g of 4 (1-oxo-2-bromoethyl)-n-hexylbenzene were dissolved in 200 ml of ethanol under heating and stirring. Then 80 ml of 30% aqueous ammonia was added dropwise thereto within approximately 10 minutes while maintaining the material temperature at 50° to 60° C. The resulting mixture was stirred at the same temperature for five hours and then 40 ml of 305 aqueous ammonia was further added. After stirring for additional five hours, the reaction mixture was cooled to room temperature. 60 ml of a 35% aqueous solution of hydrogen peroxide was added thereto and the obtained mixture was stirred for five hours. Further 60 ml of a 355 aqueous solution of hydrogen peroxide was added thereto and the mixture was stirred for additional five hours. After the completion of the reaction, the precipitate thus formed was filtered, washed thoroughly with water and dried. Yield: 8.2 g.

When analyzed by silica gel normal phase thin layer chromatography, this crude product comprised three components which shows Rf values of 0.8:0.5:0.0.

This crude reaction product was subjected to silica gel column chromatography (eluent: hexane/ethyl acetate) to thereby separate the aimed component (Rf=0.5 in the above thin layer chromatography). Yield: 2.61 g.

The reaction product thus separated was recrystallized from acetone. Thus 2.37 g of the title compound was obtained.

Phase transition temperature:
138.3° C. (C→$S_C$);

143.5° C. ($S_C \rightleftarrows S_A$);
167.1° C. ($S_A \rightleftarrows N$); and
184.4° C. ($N \rightleftarrows I$).

EXAMPLE 2

Preparation of 2-(3-fluoro-4-n-nonyloxyphenyl)-5-(4-n-hexylphenyl)-pyrazine (compound No. 8 in Table 1)

0.5 g of the 2-(3-fluoro-4-methoxyphenyl)-5-(4-n-hexylphenyl)pyrazine obtained in Example 1 was added to 50 ml of acetic acid. To the resulting mixture, was added 50 ml of a 47% hydrobromic acid. The obtained mixture was stirred under reflux for eight hours.

After evaporating volatile components, the residue was dried under reduced pressure to thereby give 0.48 g of crude 2-(3-fluoro-4-hydroxyphenyl)-5-(4-n-hexylphenyl)pyrazine. Since this product showed a single spot in thin layer chromatography, no purification was effected any more.

0.35 g of the crude 2-(3-fluoro-4-hydroxyphenyl)-5(4-n-hexylphenyl)pyrazine was dissolved in 3 ml of dimethyl sulfoxide and 3 ml of tetrahydrofuran. To the resulting solution, was added 0.12 g of potassium-tert-butoxide. The obtained mixture was stirred at room temperature for 30 minutes and then 0.22 g of n-nonyl bromide was added thereto. The mixture was stirred at room temperature for additional five hours. Then the reaction mixture was diluted with ethyl acetate, washed with dilute hydrochloric acid and with a 30% aqueous solution of sodium hydroxide and the repeatedly washed with water until the washing liquor showed a pH value of approximately 7. Then the ethyl acetate phase was dehydrated over sodium sulfate and the solvent was distilled off. Thus 0.48 g of a crude reaction product was obtained. The crude reaction product was purified by silica gel column chromatography and recrystallized from acetone. Thus 0.41 g of the title compound was obtained.

Phase transition temperature:
93.0° C. ($C \rightarrow S_C$);
170.5° C. ($S_C \rightleftarrows S_A$); and
172.2° C. ($S_A \rightleftarrows I$).

EXAMPLE 3

2-(3-Fluoro-4-ethoxyphenyl)-5-(4-n-hexylphenyl)-pyrazine (compound No. 2 in Table 1) was obtained in the same manner as described in Example 2.

Phase transition temperature:
117.1° C. ($C \rightarrow S_C$);
174.2° C. ($S_C \rightleftarrows S_A$);
183.0° C. ($S_A \rightleftarrows N$); and
194.2° C. ($N \rightleftarrows I$).

EXAMPLE 4

2-(3-Fluoro-4-n-propoxyphenyl)-5-(4-n-hexylphenyl)pyrazine (compound No. 3 in Table 1) was obtained in the same manner as described in Example 2.

Phase transition temperature:
119.7° C. ($C \rightarrow S_C$);
173.9° C. ($S_C \rightleftarrows S_A$);
181.8° C. ($S_A \rightleftarrows N$); and
185.6° C. ($N \rightleftarrows I$).

EXAMPLE 5

2-(3-Fluoro-4-n-butoxyphenyl)-5-(4-n-hexylphenyl)-pyrazine (compound No. 4 in Table 1) was obtained in the same manner as described in Example 2.

Phase transition temperature:
106.0° C. ($C \rightleftarrows S_C$);
181.0° C. ($S_C \rightleftarrows S_A$);
185.5° C. ($S_A \rightleftarrows N$); and
187.0° C. ($N \rightleftarrows I$).

EXAMPLE 6

2-(3-Fluoro-4-n-pentyloxyphenyl)-5-(4-n-hexylphenyl)pyrazine (compound No. 5 in Table 1) was obtained in the same manner as described in Example 2.

Phase transition temperature:
101.6° C. ($C \rightarrow S_C$);
177° C. ($S_C \rightleftarrows S_A$); and
181.3° C. ($S_A \rightleftarrows N$).

EXAMPLE 7

2-(3-Fluoro-4-n-hexyloxyphenyl)-5-(4-n-hexylphenyl)pyrazine (compound No. 6 in Table 1) was obtained in the same manner as described in Example 2.

Phase transition temperature:
95.6° C. ($C \rightarrow S_C$);
178.2° C. ($S_C \rightleftarrows S_A$);
180.1° C. ($S_A \rightleftarrows N$); and
181.1° C. ($N \rightleftarrows I$).

EXAMPLE 8

2-(3-Fluoro-4-n-heptyloxyphenyl)-5-(4-n-hexylphenyl)pyrazine (compound No. 7 in Table 1) was obtained in the same manner as described in Example 2.

Phase transition temperature:
93.8° C. ($C \rightarrow S_C$);
175.3° C. ($S_C \rightleftarrows S_A$); and
176.6° C. ($S_A \rightleftarrows N$).

EXAMPLE 9

Preparation of 2-(3-fluoro-4-methoxyphenyl)-5-(4-n-nonylphenyl)-pyrazine (compound No. 9 in Table 1)

The procedure of Example 1 was repeated except that the 4-(1-oxo-2-bromoethyl)-n-hexylbenzene was substituted with 34.5 g of 4-(1-oxo-2-bromoethyl)-n-nonylbenzene and that the reactants were dissolved in 400 ml of ethanol. Thus 3.98 g of the title compound was obtained.

Phase transition temperature:
133.3° C. ($C \rightarrow S_A$);
163.7° C. ($S_A \rightleftarrows N$); and
173.3° C. ($N \rightleftarrows I$);

EXAMPLE 10

Preparation of 2-(3-fluoro-4-n-hexyloxyphenyl)-5-(4-n-nonylphenyl)-pyrazine (compound No. 14 in Table 1)

0.5 g of the 2-(3-fluoro-4-methoxyphenyl)-5-(4-n-nonylphenyl)pyrazine obtained in Example 9 was treated in the same manner as described in Example 2 to thereby give 0.49 g of crude 2-(3-fluoro-4-hydroxyphenyl)-5-(4-n-nonylphenyl)pyrazine.

The whole of this crude product was dissolved in 4 ml of dimethyl sulfoxide and 4 ml of tetrahydrofuran and 0.15 g of potassium-tert-botoxide was added thereto. The obtained mixture was stirred at room temperature for 15 minutes and then 0.22 g of n-hexyl bromide was added thereto. After stirring for five hours, the reaction mixture .was treated in the same manner as described in Example 2. Thus 0.52 g of the title compound was obtained.

Phase transition temperature:
86.6° C. (C→S$_C$);
175.4° C. (S$_C$⇌S$_A$); and
176.7° C. (S$_A$⇌I).

EXAMPLE 11

2-(3-Fluoro-4-ethoxyphenyl)-5-(4-n-nonylphenyl)-pyrazine (compound No. 10 in Table 1) was obtained in the same manner as described in Example 10.
Phase transition temperature:
107.8° C. (C→S$_C$);
159.2° C. (S$_C$⇌S$_A$);
181.0° C. (S$_A$⇌N); and
184.2° C. (N⇌I).

EXAMPLE 12

2-(3-Fluoro-4-n-propoxyphenyl) 5-(4-n-nonylphenyl)pyrazine (compound No. 11 in Table 1) was obtained in the same manner as described in Example 10.
Phase transition temperature:
103.2° C. (C→S$_C$);
163.4° C. (S$_C$⇌S$_A$); and
179.4° C. (S$_A$⇌I).

EXAMPLE 13

2-(3-Fluoro-4-n-butoxyphenyl)-5-(4-n-nonylphenyl)-pyrazine (compound No. 12 in Table 1) was obtained in the same manner as described in Example 10.
Phase transition temperature:
90.2° C. (C→S$_C$);
172.6° C. (S$_C$⇌S$_A$);
182.7° C. (S$_A$⇌N); and
182.8° C. (N⇌I).

EXAMPLE 14

2-(3-Fluoro-4-n-pentyloxyphenyl)-5-(4-n-nonylphenyl)pyrazine (compound No. 13 in Table 1) was obtained in the same manner as described in Example 10.
Phase transition temperature:
92.7° C. (C→S$_C$);
174.9° C. (S$_C$⇌S$_A$); and
178.5° C. (S$_A$⇌I).

EXAMPLE 15

2-(3-Fluoro-4-n-heptyloxyphenyl)-5-(4-n-nonylphenyl)pyrazine (compound No. 15 in Table 1) was obtained in the same manner as described in Example 10.
Phase transition temperature:
92.0° C. (C→S$_C$); and
175.0° C. (S$_C$⇌I).

EXAMPLE 16

2-(3-Fluoro-4-n-octyloxyphenyl)-5-(4-n-nonylphenyl)pyrazine (compound No. 16 in Table 1) was obtained in the same manner as described in Example 10.
Phase transition temperature:
92.2° C. (C→S$_C$); and
174.1° C. (S$_C$⇌I).

EXAMPLE 17

2-(3-Fluoro-4-n-nonyloxyphenyl)-5-(4-n-nonylphenyl)pyrazine (compound No. 17 in Table 1) was obtained in the same manner as described in Example 10.

Phase transition temperature:
94.5° C. (C→S$_C$); and
171.7° C. (S$_C$⇌I).

EXAMPLE 18

2-[3-Fluoro-4-(2-methylbutyloxy)phenyl]-5-(4-n-nonylphenyl)pyrazine (compound No. 18 in Table 1) was obtained in the same manner as described in Example 10.
Phase transition temperature:
91.2° C. (C→S$_C$);
148.2° C. (S$_C$⇌S$_A$); and
151.9° C. (S$_A$⇌N).

EXAMPLE 19

Starting from 24.7 g of 2-fluoro-4-(1-oxo-2-bromoethyl)anisole and 27.8 g of 4-(1-oxo-2-bromoethyl)-n-heptylbenzene, 2.30 g of 2-(3-fluoro-4-methoxyphenyl)-5-(4-n-heptylphenyl)pyrazine (compound No. 19 in Table 1) was obtained in the same manner as described in Example 1.
Phase transition temperature:
134.5° C. (C→S$_A$);
165.7 C (S$_A$⇌N); and
182.0° C. (N⇌I).

EXAMPLE 20

The methyl group of the compound No. 19 in Table 1, which was obtained in the above Example 19, was removed in the same manner as described in Example 2. The resulting compound was reacted with 4-methylhexyl bromide to thereby give 2-[3-fluoro-4-(4-methylhexyloxy)phenyl]-5-(4-n-heptylphenyl)pyrazine (compound No. 20 in Table 1).
Phase transition temperature:
85.0° C. (C→S$_C$); and
165.0° C. (S$_C$⇌I);

EXAMPLE 21

Synthesis of 2 (3-fluoro-4-methoxyphenyl)-5-(4-heptylpheny)pyrimidine (compound No. 21 in Table 1)

(a) Synthesis of 3-fluoro-4-methoxybenzamidine hydrochloride:
306 g of 2-fluoroanisole was dissolved in 750 ml of chloroform. To the resulting solution, was added dropwise 389 g of bromine under stirring at room temperature. After the completion of the addition, the reaction mixture was heated under reflux for nine hours and then allowed to cool to room temperature. The mixture was washed with 500 ml of a 5% aqueous solution of sodium hydroxide and then the organic layer was washed with 500 ml portions of water thrice. The organic layer was separated and dried over anhydrous sodium sulfate. After distilling off the solvent, the residue was purified by distillation (main fraction: 14 mmHg, 98°-100° C.) to thereby give 454 g of 2-fluoro-4-bromoanisole. Yield: 91%.

20 g of the 2-fluoro-4-bromoanisole thus obtained and 9.8 g of copper cyanide were dissolved in 100 ml of dimethyl formamide and heated under reflux for ten hours. To the reaction mixture, was added an aqueous solution of 20 g of ferric chloride in 100 ml of water. The reaction mixture was allowed to cool to room temperature and the reaction product was extracted with toluene. The organic layer was successively washed with water, a saturated aqueous solution of sodium carbonate and a saturated aqueous solution of common salt. Then the organic layer was separated. The extract was dried over anhydrous sodium sulfate and the solvent was distilled off. The residue was purified by silica gel column chromatography (developing solvent: hexane:ethyl acetate=10:1) and further recrystallized from ethanol. Thus 10.0 g of 3-fluoro-4-methoxybenzonitrile was obtained. Yield: 68%.

To the 3-fluoro-4-methoxybenzonitrile thus obtained, were added 150 ml of ether and 3.7 g of ethanol. The obtained solution was cooled to 10° C. or below and hydrogen chloride was bubbled thereto until saturation was achieved. Then the mixture was stirred at room temperature for three days. The reaction mixture was cooled and the precipitate thus formed was filtered and washed with a small amount of ether. Thus 8.5 g of imino ester hydrochloride was obtained. Yield: 60%.

8.5 g of the imino ester hydrochloride thus obtained was dissolved in 200 ml of ethanol. The obtained solution was cooled to 15° C. or below and ammonia gas was bubbled thereto until saturation was achieved. The mixture was then stirred at room temperature for three days. The solvent was distilled off under reduced pressure until crystals were precipitated. After adding 300 ml of ether, the crystals were filtered and vacuum-dried. Thus 4.1 g of 3-fluoro-4-methoxybenzamidine hydrochloride was obtained. Yield: 55%.

(b) Synthesis of 3-dimethylamino-2-(4-heptylphenyl)-2-propene-N,N-dimethyliminium perchlorate 41.9 g of p-n-heptylacetophenone, 12.3 g of sulfur and 33.4 g of morpholine were mixed together. The obtained mixture was heated under reflux for six hours. The reaction mixture was cooled to 0° C. and 300 ml of methanol was added thereto. The crystals thus precipitated were filtered and vacuum-dried. Thus 56.1 g of 4-[2-(4-heptylphenyl)-1-thioxoethyl]morpholine was obtained. Yield: 91%.

To 56.1 g of the 4-[2-(4-heptylphenyl)-1-thioxoethyl]-morpholine thus obtained, were added 300 ml of triethylene glycol, 50 ml of water and 37.3 g of potassium hydroxide. The resulting mixture was heated under reflux for six hours and then allowed to cool to room temperature. Then 10% hydrochloric acid was added thereto by portions until the pH value of the solution became slightly acidic. The reaction product was extracted with 300 ml of ethyl acetate and the organic layer was washed with water until the aqueous layer became neutral. Then the organic layer was separated and dried over anhydrous sodium sulfate. After distilling off the solvent, the residue was recrystallized from hexane. Thus 28.0 g of p-heptylphenylacetic acid was obtained. Yield: 18%.

31.2 g of dimethylformamide was cooled to 5° C. and 39.4 g of phosphorus oxychloride was added dropwise thereto while stirring at the same temperature. The obtained mixture was further stirred at −5° C. for 30 minutes. The reaction mixture was cooled to −10° C. and 20 g of p-n-heptylphenyl acetic acid was added thereto. The resulting mixture was stirred at room temperature for one hour, at 60° C. for two hours and at 80° C. for five hours and then cooled to 0° C. Subsequently 300 ml of water was added dropwise thereto. After the completion of the addition, 19.1 g of magnesium perchlorate was added thereto. The crystals thus precipitated were filtered, washed with water, extracted with ether and vacuum-dried. Thus 31.9 g of 3-dimethylamino-2-(4-heptylphenyl)-2-propene-N,N-dimethyliminium perchlorate was obtained. Yield: 95%.

(c) Synthesis of 2-(3-fluoro-4-methoxyphenyl)-5-(4-heptylphenyl)pyrimidine:

2.7 g of 3-fluoro-4-methoxybenzamidine hydrochloride and 5.2 g of 3-dimethylamino-2-(4-heptylphenyl)-2propene-N,N-dimethyliminium perchlorate were dissolved in 50 ml of ethanol. To the resulting solution, was added dropwise a sodium ethoxide solution prepared from 1.5 g of sodium and 50 ml of ethanol. After the completion of the addition, the mixture was heated under reflux for six hours. The reaction mixture was allowed to cool to room temperature and 100 ml of water was added thereto. The crystals thus precipitated were filtered, purified by silica gel column chromatography (developing solvent: toluene) and recrystallized from ethanol. Thus 2.7 g of 2-(3-fluoro-4-methoxyphenyl)-5-(4-heptylphenyl)pyrimidine was obtained. Yield: 54%.

Phase transition temperature:
70.0° C. (C→$S_A$); and
176.5° C. ($S_A \rightleftarrows I$).

EXAMPLE 22

Synthesis of 2-(3-fluoro-4-hexyloxyphenyl)-5-(4-heptylphenyl)-pyrimidine (compound No. 22 in Table 1)

(a) Synthesis of 2-(3-fluoro-4-hydroxyphenyl)-5-(4-heptylphenyl)pyrimidine:

2.5 g of the 2-(3-fluoro-4-methoxyphenyl)-5-(4-heptylpheny)pyrimidine obtained in Example 1 was dissolved in a mixture of 200 ml of acetic acid and 100 ml of 47% hydrobromic acid. The obtained solution was heated under reflux for 18 hours. The reaction mixture was allowed to cool to room temperature and 500 ml of water was added thereto. The crystals thus precipitated were filtered. The product thus obtained was purified by column chromatography (developing solvent: hexane: ethyl acetate=5:1) to thereby give 2.1 g of 2-(3-fluoro-4-hydroxyphenyl)-5-(4-heptylphenyl)pyrimidine. Yield: 87%.

(b) Synthesis of 2-(3-fluoro 4-hexyloxyphenyl)-5-(4-heptylphenyl)pyrimidine:

0.5 g of 2-(3-fluoro-4-hydroxyphenyl)-5-(4-heptylphenyl)pyrimidine and 0.185 g of potassium-tertbutoxide were dissolved in 20 ml of dimethyl sulfoxide. The resulting solution was stirred at room temperature for 30 minutes and then 0.295 of n-hexyl bromide was added dropwise thereto. After the completion of the addition, the mixture was stirred at room temperature for six hours. Then 100 ml of ethyl acetate and 100 ml of water were added to the reaction mixture and the organic layer was repeatedly washed with water until the pH value of the aqueous layer became neutral. Subsequently the organic layer was separated and dried over anhydrous sodium sulfate. After distilling off the solvent, the residue was purified by silica gel column chromatography (developing solvent: toluene) and then recrystallized from ethanol. Thus 0.467 g of 2-(3-fluoro-4-hexyloxyphenyl)-5-(4-heptylphenyl)pyrimidine was obtained. Yield: 74%.

Phase transition temperature:
$S_A$-I=181° C.; and
$S_C$-$S_A$=143.5° C.
m.p.: 80.5° C.

EXAMPLES 23 TO 25

The compounds No. 23 to No. 25 shown in Table 1 were synthesized each in the same manner as described in Example 22.

EXAMPLE 26

Synthesis of 2-(2-fluoro-4-octyloxyphenyl)-5-(4-octylphenyl)pyrimidine (compound No. 26 in Table 1)

(a) Synthesis of 2-fluoro-4-n-octyloxypenylamidine hydrochloride:

60 g of 3-fluoro-4-cyanophenol and 16 g of potassium hydroxide were dissolved in a solvent mixture of 600 ml of ethanol and 60 ml of water. To the resulting solution, was added dropwise 55.8 g of octyl bromide. After the completion of the addition, the obtained mixture was refluxed for six hours and then allowed to cool to room temperature. The solvent was distilled off and 300 ml of ethyl acetate was added to the residue. The organic layer was washed with water until the aqueous layer became neutral. The organic layer was dehydrated over anhydrous sodium sulfate and the solvent was distilled off. After purifying by distillation (main fraction: 0.5 mmHg, 157° to 160° C.), 63 g of 2-fluoro-4-octyloxybenzonitrile was obtained. Yield: 58%. 63 g of the 2-fluoro-4-octyloxybenzonitrile thus obtained was dissolved in 70 ml of absolute ether and 12.7 g of absolute ethanol was added thereto. The obtained mixture was cooled to $-10°$ C. Then hydrogen chloride gas was bubbled therein for 30 minutes under stirring. After confirming that no hydrogen chloride was absorbed any more, the mixture was stirred at room temperature for 72 hours. 400 ml of absolute ether was added to the mixture. The crystals thus precipitated were filtered and vacuum-dried to thereby give 42 g of imino ester hydrochloride. Yield: 52%.

Then ammonia gas was bubbled into 300 ml of absolute ethanol at 0° C. for 30 minutes and 42 g of the imino ester hydrochloride thus obtained was added thereto. The obtained mixture was stirred at room temperature for 72 hours. 300 ml of absolute ether was added thereto. The crystals thus precipitated were filtered and vacuum-dried. Thus 24 g of 2-fluoro-4-octyloxyphenylamidine hydrochloride was obtained. Yield: 60%.

(b) Synthesis of 3-dimethylamino-2-(4-octylphenyl)-2-propene-N,N-dimethyliminium perchlorate:

98.3 g of p-n-octylacetophenone and 27.2 g of sulfur were dissolved in 73.9 g of morpholine. The obtained solution was refluxed for four hours and then cooled to 0° C. After adding 300 ml of methanol, the crystals thus precipitated were filtered and vacuum-dried. Thus 117 g of 4-[2-(4-octylphenyl)-1-thioxoethyl]-morpholine was obtained. Yield: 83%.

117 g of the 4-[2-(4-octylphenyl)-1-thioxoethyl]-morpholine was added to 250 ml of ethanol and dissolved therein. 50 ml of water and 46.3 g of potassium hydroxide were added to the obtained solution and the mixture was refluxed for three hours and then allowed to cool to room temperature. Then 10% hydrochloric acid was added thereto by portions until the mixture became acidic. After adding 500 ml of ethyl acetate, the organic layer was washed with water until the aqueous layer became neutral. The organic layer was separated and the solvent was distilled off. To the residue, were added 500 ml of triethylene glycol, 70 ml of water and 77.2 g of potassium hydroxide and the resulting mixture was refluxed for four hours. After allowing to cool to room temperature, 10% hydrochloric acid was added thereto by portions until it became acidic. After adding 500 ml of ethyl acetate, the organic layer was washed with water until the aqueous layer became neutral. The organic layer was separated and dehydrated over anhydrous sodium sulfate. The solvent was distilled off and the residue was recrystallized from hexane. Thus 65.5 g of p-octylphenylacetic acid was obtained. Yield: 74%.

Subsequently 73.2 g of dimethylformamide was cooled to $-5°$ C. and 92 g of phosphorus oxychloride was added dropwise thereto under stirring. After stirring at $-5°$ C. for 30 minutes, the mixture was cooled to $-10°$ C. and 49.6 g of p-octylphenylacetic acid was added thereto. The obtained mixture was stirred at room temperature for one hour, at 60° C. for two hours and at 80° C. for five hours and then cooled to 0° C. To the mixture, was added dropwise 400 ml of water. Then 44.8 g of magnesium perchlorate was further added thereto. The crystals thus precipitated were filtered, washed with ether and vacuum-dried. Thus 81 g of 3-dimethylamino-2-(4-octylphenyl)-2-propene-N,N-dimethyliminium perchlorate was obtained. Yield: 99%.

(c) Synthesis of 2-(2-fluoro-4-octyloxyphenyl)-5-(4-octylphenyl)pyrimidine:

1.56 g of the 2-fluoro-4-octyloxyphenylamidine hydrochloride obtained in (a) and 2 g of the 3-dimethylamino-2-(4-octylphenyl)-2-propene-N,N-dimethyliminium perchlorate obtained in (b) were dissolved in 50 ml of absolute ethanol. Then a sodium ethoxide solution prepared from 0.6 g of sodium in 50 ml of absolute ethanol was added dropwise thereto and the resulting mixture was refluxed for four hours. After allowing to cool to room temperature, 50 ml of water was added thereto. The crystals thus precipitated were filtered, washed with water and vacuum-dried. These crystals were purified by silica gel column chromatography (developing solvent: benzene) and recrystallized from ethanol. Thus 1.27 g of 2-(2-fluoro-4-octyloxyphenyl)-5-(4-octylphenyl)pyrimidine was obtained. Yield: 53%.

Phase transition temperature:
N-I=150° C.; and
S$_C$-N=133° C.
m.p.: 75° C.

EXAMPLES 27 TO 29

The compounds No. 27 to No. 29 shown in Table 1 were synthesized each in the same manner as described in Example 26.

EXAMPLE 30

Synthesis of 2-[2-fluoro-4-(4-methylhexyloxy)-phenyl]-5-(4-octylphenyl)pyrimidine (compound No. 30 in Table 1)

(a) Synthesis of 2-fluoro-4-hydroxyphenylamidine hydrochloride 35 g of 2-fluoro-4-octyloxybenzonitrile was dissolved in 200 ml of absolute ether and 14.4 ml of absolute ethanol and cooled to 0° C. Hydrogen chloride gas was bubbled thereto for 30 minutes under stirring. After confirming that no hydrogen chloride gas was absorbed any more, the mixture was stirred at room temperature for 96 hours. To the reaction mixture, was added 200 ml of absolute ether. The crystals thus precipitated were filtered and dried under reduced pressure. Thus 54.2 g of imino ester hydrochloride of the formula (X) wherein

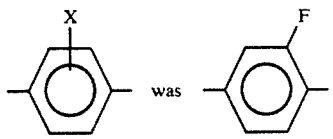 was obtained.

Yield: 97%.

Subsequently ammonia gas was bubbled into 200 ml of absolute ethanol at 0° C. for 30 minutes to thereby dissolve therein. Then 54.2 g of the imino ester hydrochloride obtained above was added thereto and the mixture was stirred at room temperature for 96 hours. 500 ml of absolute ether was added thereto and the crystals thus precipitated were filtered and dried under reduced pressure. Thus 45.5 g of 2-fluoro-4-hydroxyphenylamidine hydrochloride was obtained. Yield: 97%.

(b) Synthesis of 2-(2-fluoro-4-hydroxy)phenyl-5-(4-octylphenyl)pyrimidine:

8.54 g of the 2-fluoro-4-hydroxyphenylamidine hydrochloride obtained in (a) and 20 g of the 3-dimethylamino-2-(4-octylphenyl)-2-propene-N,N-dimethyliminium perchlorate obtained in (b) in the above Example 26 were dissolved in 200 ml of absolute ethanol. Then a sodium ethoxide solution prepared from 100 ml of absolute ethanol and 16.8 g of sodium was added dropwise thereto. The obtained mixture was heated under reflux for six hours and allowed to cool to room temperature. After adding 500 ml of water, the crystals thus precipitated were filtered, washed with water, vacuum-dried and recrystallized from toluene. Thus 11.1 g of 2-(2-fluoro-4-hydroxyphenyl)-5-(4-octylphenyl)pyrimidine crystals were obtained. Yield: 71%. m.p.: 167° C.

IR: 1620, 1580, 1425, 1340, 1315, 1270, 1230, 1160, 1115, 840 and 820 cm$^{-1}$.

(c) Synthesis of the title compound:

1.0 g of the 2-(2-fluoro-4-hydroxy)phenyl-5-(4-octylphenyl)pyrimidine obtained in (b) was dissolved in 10 ml of dimethylformamide. To the resulting solution, was slowly added 0.37 g of potassium-tert-butoxide. The obtained mixture was stirred at room temperature.

To the mixture, was added dropwise 0.928 g of 4-methylhexyl tosylate, which had been obtained by reacting diethyl malonate with 2-methylbutyl bromide, decarboxylating the obtained product, reducing the product with LiAlH$_4$ and finally tosylating the product with tosyl chloride.

After the completion of the addition, the mixture was allowed to react at 50° C. for six hours and then allowed to cool to room temperature. To the reaction mixture, were added water and ether. Further dilute hydrochloric acid was added thereto until the aqueous layer became neutral. The organic layer was washed with water and then with a saturated solution of common salt and dehydrated over anhydrous sodium sulfate. After distilling off the solvent, the residue was purified by silica gel column chromatography and then recrystallized from ethanol. Thus 0.58 g of 2-[2-fluoro-4-(4-methylhexyloxy)phenyl]-5-(4-octylphenyl)pyrimidine was obtained in the form of white crystals. Yield: 46%. The phase transition temperature of this product are shown in Table 1.

IR: 1610, 1580, 1510, 1435, 1340, 1285, 1160, 1130, 1015, 845, 810 and 790 cm$^{-1}$.

EXAMPLE 31

The compound No. 31 shown in Table 1 was obtained by the same manner as described in Example 30 except that the 4-methylhexyl tosylate was replaced with 4-mehylheptyl tosylate.

EXAMPLE 32

The compound No. 32 shown in Table 1 was obtained by the same manner as described in Example 30 except that the 4-methylhexyl tosylate was replaced with 8-methyldecyl tosylate.

EXAMPLE 33

The compound No. 33 shown in Table 1 was obtained by the same manner as described in Example 30 except that the 4-methylhexyl tosylate was replaced with 8-methylnonyl tosylate.

EXAMPLE 34

The compound No. 34 shown in Table 1 was obtained by the same manner as described in Example 30 except that the 4-methylhexyl tosylate was replaced with 6-methylnonyl tosylate.

EXAMPLE 35

The compound No. 35 shown in Table 1 was obtained by the same manner as described in Example 30 except that the p-n octylacetophenone was replaced with p-n-heptylacetophenone and the 4-methylhexyl tosylate was replaced with 2 methylbutyl tosylate.

EXAMPLE 36

50% by weight of the compound obtained in Example 2 (Compound No. 8 in Table 1) was mixed with 50% by weight of the compound obtained in Example 7 (Compound No. 6 in Table 1) to thereby give a liquid crystal mixture (B). Table 3 shows the phase transition temperatures of the compounds No. 6 and No. 8 as well as those of the liquid crystal mixture (B).

TABLE 3

| | Phases and Phase Transition Temperatures (°C.) | | | | |
|---|---|---|---|---|---|
| | C | S$_C$ | S$_A$ | N | I |
| Cpd. No. 6 | •95.6 | •178.2 | •180.1 | •181.1 | • |
| Cpd. No. 8 | •93.0 | •170.5 | •172.2 | — | • |
| Liquid Crystal Mixture (B) | •80 | •172 | •176 | — | • |

Table 3 obviously indicates that the mixing of the compounds No. 6 and No. 8 causes a considerable decrease in the melting point. It may be understood, therefore, that a liquid crystal mixture showing an S$_C$ phase over a wide temperature range can be obtained thereby.

EXAMPLE 37

The compound obtained in Example 14 (Compound No. in Table 1) was mixed with 4-[2-(trans-4-n-propylcyclohexyl)-ethyl]phenyl 4-decyloxy-3-fluorobenzoate (Compound No. R-1 described in JP-A-63-188653) at a ratio by weight of 26:74 or 57:43. Thus liquid crystal mixtures (C) and (D) were obtained. Table 4 shows the phase transition temperatures of the compounds No. 13 and No. R-1 as well as those of the liquid crystal mixtures (C) and D.

TABLE 4

| | Phases and Phase Transition Temperatures (°C.) | | | |
|---|---|---|---|---|
| | C | $S_c$ | $S_A$ | N | I |
| Cpd. No. 13 | °92.7 | °174.9 | °178.5 | — | ° |
| Cpd. No. R-1 | °55.2 | °88.5 | — | °135.1 | ° |
| Liquid Crystal Mixture (C) | °51 | °108 | — | °142 | ° |
| Liquid Crystal Mixture (D) | °63 | °129 | °142 | °153 | ° |

Table 4 obviously indicates that the compound No. 13 shows an $S_C$ phase over a wide temperature range; that it can show an $S_A$ phase within a higher temperature range than that of the $S_C$ phase when mixed with the compound No. R-1 which shows no $S_A$ phase; and that it shows no higher-order smectic phase than that of the $S_C$ phase. It can be understood, therefore, that these liquid crystal mixtures suffer from no irregular orientation of the $S_C$ phase in the formation of a cell. It can be further understood that the compound No. 13 shows a significant decrease in melting point when mixed with the compound No. R-1 and that it can provide a liquid crystal mixture showing an $S_C$ phase over a wide temperature range.

EXAMPLE 38

The compound obtained in Example 16 (Compound No. 16 in Table 1) was mixed with the compound obtained in Example 27 (Compound No. 27 in Table 1) at a ratio by weight of 51:49 or 14.5:85.5. Thus liquid crystal mixtures (E) and (F) were obtained. Table 5 shows the phase transition temperatures of the compounds No. 16 and No. 27 as well as those of the liquid crystal mixtures (E) and (F).

TABLE 5

| | Phases and Phase Transition Temperatures (°C.) | | | |
|---|---|---|---|---|
| | C | $S_C$ | $S_A$ | N | I |
| Cpd. No. 16 | °92.2 | °174.1 | — | — | ° |
| Cpd. No. 27 | °78.5 | °131.0 | — | °156.0 | ° |
| Liquid Crystal Mixture (E) | °62 | °158 | °160 | °164 | ° |
| Liquid Crystal Mixture (F) | °64 | °139 | °139.5 | °158 | ° |

Table 5 obviously indicates that the mixing of the compounds No. 16 and No. 27 results in a liquid crystal mixture showing an $S_A$ phase, which is observed neither in these compounds. Thus it can be understood that the liquid crystal mixture thus obtained suffers from no irregular orientation of the $S_C$ phase in the formation of a display cell. It can be further understood that the compound No. 16 shows a considerable decrease in the melting point when mixed with the compound No. 27; and that it can thus provide a liquid crystal mixture showing an $S_C$ phase over a wide range of temperature.

EXAMPLE 39

63% by weight of the compound obtained in Example 10 (Compound No. 14 in Table 1) was added to a liquid crystal mixture (G) comprising a bicyclic pyrimidine derivative and a bicyclic alkoxyphenyl benzoate derivative to thereby give a liquid crystal mixture (H). Table 6 shows the phase transition temperatures of the compound No. 14 as well as those of the liquid crystal mixtures (G) and (H).

TABLE 6

| | Phases and Phase Transition Temperatures (°C.) | | | |
|---|---|---|---|---|
| | $S_C$ | $S_A$ | N | I |
| Cpd. No. 14 | °175.4 | °176.7 | — | ° |
| Liquid Crystal Mixture (G) | °56 | — | °72 | ° |
| Liquid Crystal Mixture (H) | °62 | °64 | °77 | ° |

The liquid crystal mixture (G) comprising 24% of

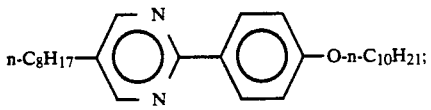

27% of

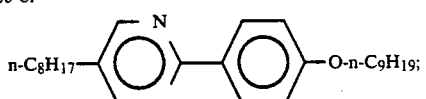

6% of

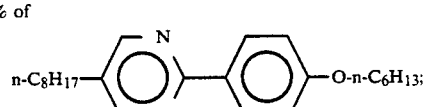

3% of

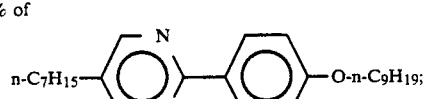

10% of

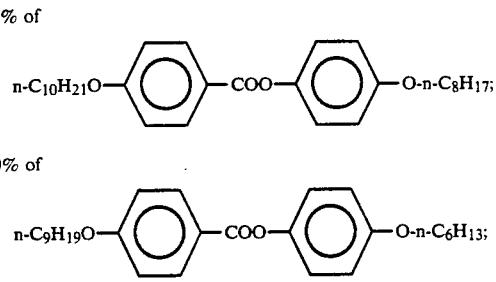

10% of

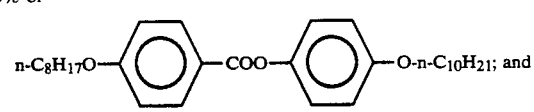

10% of

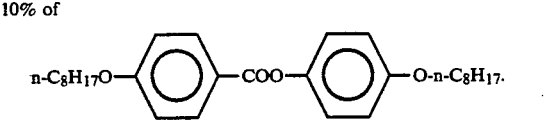

10% of n-C$_8$H$_{17}$O—⟨◯⟩—COO—⟨◯⟩—O-n-C$_8$H$_{17}$.

Table 6 obviously indicates that the addition of the compound No. 14 can give a liquid crystal mixture showing an $S_A$ phase which is never observed in the liquid crystal mixture (G). Thus it can be understood that the obtained liquid crystal mixture suffers from no irregular orientation of the $S_C$ phase in the formation of a display cell. Further it can be understood that the addition of the compound No. 14 can elevate the upper limit of the $S_C$ phase of the liquid crystal mixture by 6° C.; and thus a liquid crystal mixture showing an $S_C$ phase over a wide temperature range can be obtained thereby.

EXAMPLE 40

A liquid crystal mixture comprising 25% of

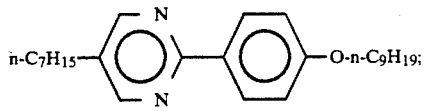

25% of

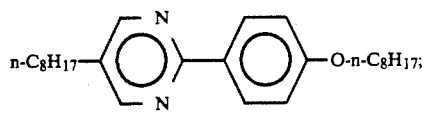

25% of

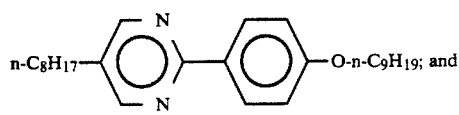

25% of

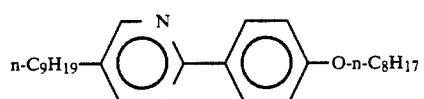

showed an Sc phase at 19° to 55° C. 85% of this liquid crystal mixture was mixed with 15% of the compound No. 24 in Table 1 obtained in Example 24. The obtained liquid crystal mixture showed an Sc phase at 4° to 62° C. Thus a liquid crystal composition capable of showing an Sc phase over a wide temperature range involving room temperature was obtained thereby.

EXAMPLE 41

A liquid crystal mixture comprising 17% of

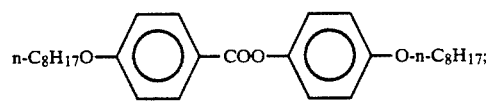

17% of

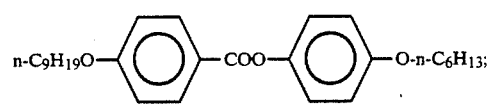

33% of

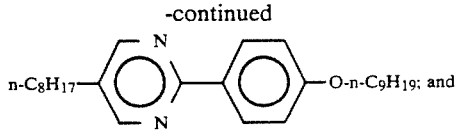

33% of

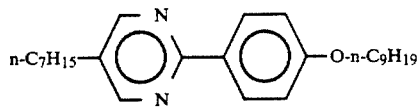

shows an Sc phase at 19° to 54° C. 60% of this liquid crystal mixture was mixed with 25% of the compound No. 26 in Table 1 obtained in Example 26 and 15 of the compound No. 29 in Table 1 obtained in Example 29. The obtained liquid crystal mixture showed an Sc phase at 5° to 78° C. Thus a liquid crystal composition capable of showing an Sc phase over a wide temperature range involving room temperature was obtained thereby.

EXAMPLE 42

A liquid crystal mixture comprising 35% of

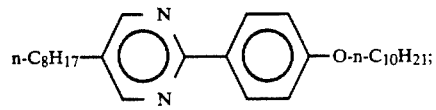

35% of

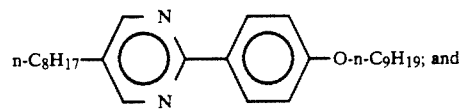

30% of

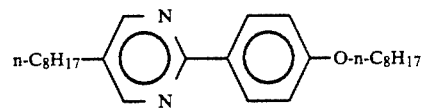

showed an Sc phase at 14° to 57° C. 85% by weight of this liquid crystal mixture was mixed with 15% weight of the compound No. 31 in Table 1 obtained in Example 31. The obtained liquid crystal mixture showed an Sc phase at 6° to 63.5° C. Thus a liquid crystal composition capable of showing an Sc phase over a wide temperature range involving room temperature was obtained thereby.

EXAMPLE 43

A liquid crystal mixture comprising 21% of

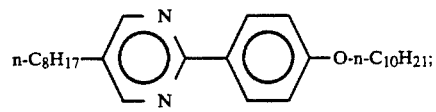

21% of

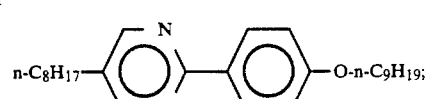

18% of

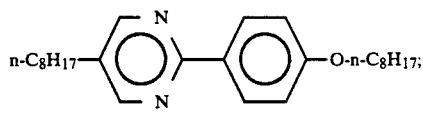

18.3% of

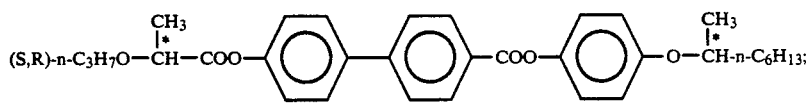

6.7% of

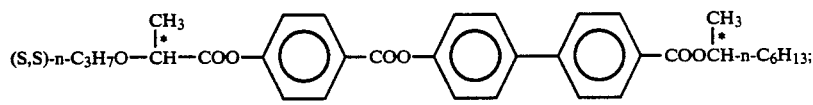

and 15% by weight of the compound No. 6 in Table 1 showed an S$_C$* phase at 62.5° C. or below.

This liquid crystal mixture was packed within a cell having about 2 μm thickness, which had been orientated, and slowly cooled form an isotropic liquid phase. Thus a highly excellent orientation was observed.

To the cell, a rectangle wave (10 Vp-p/μm, 50 Hz) was applied to thereby determine the electrooptical response speed. As a result, a high response of 25 μsec at 25° C. was confirmed.

EXAMPLE 44

A liquid crystal mixture comprising 26.3% of

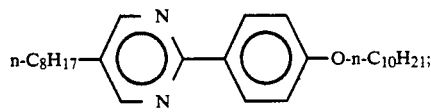

26.3% of

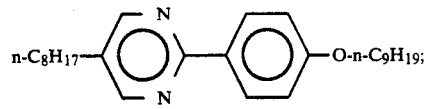

22.6% of

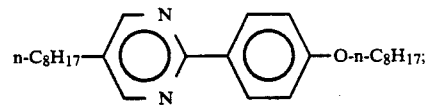

11.7% of

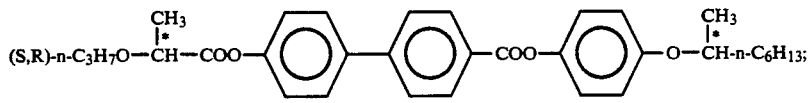

4.3% of

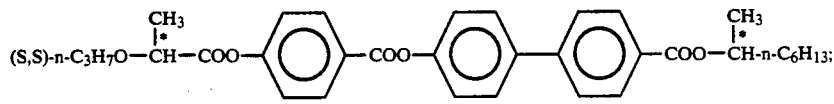

and 8.4% of the compound No. 14 in Table 1 showed S$_C$* phase 68° C. or below.

The electrooptical response speed of this liquid crystal mixture was determined in the same manner as described in Example 43. As a result, it showed a high speed response of 25 μsec at 25° C.

EXAMPLE 45

90% of the liquid crystal mixture showing an S$_C$ phase 4° to 62° C. prepared in Example 40 was mixed with 10% by weight of optically active 4'-{(S)-2-methylbutoxycarbonyl}biphenyl-4-yl 4-{(S)-2-propoxypropanoyloxy}benzoate. The obtained liquid crystal mixture showed an S$_C$* phase at 1° to 55° C. Thus a liquid crystal composition showing an S$_C$* phase over a wide temperature range involving room temperature was obtained.

EXAMPLE 46

A liquid crystal mixture comprising 23.6% of

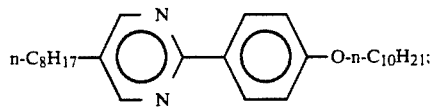

23.6% of

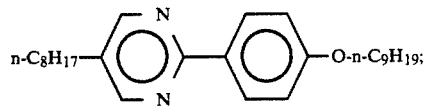

20.3% of

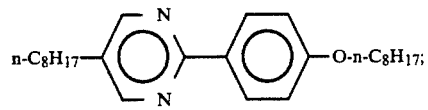

18.3% of

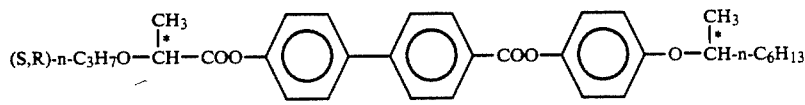

6.7% of

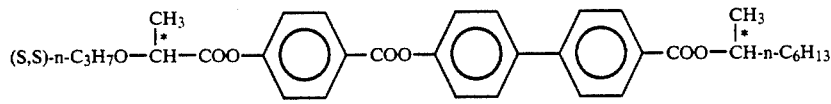

and 7.5% of the compound No. 24 in Table 1 showed an S$_C$* phase at 62° C. or below.

The electrooptical response speed of this liquid crystal mixture was determined in the same manner as described in Example 43. As a result, it showed a high speed response of 40 μsec at 25° C.

EXAMPLE 47

The procedure of Example 46 was repeated except that the compound No. 24 was replaced with the compound No. 25. The obtained liquid crystal mixture showed an S$_C$* phase at 58° C. or below.

The electrooptical response speed of this liquid crystal mixture was determined in the same manner as described in Example 43. As a result, it showed a high speed response of 55 μsec at 25° C.

EXAMPLE 48

90% of the liquid crystal mixture showing an Sc phase at 5° to 78° C. obtained in Example 41 was mixed with 10% by weight of optically active 4-[4'-dodecyloxy-4-biphenylcarbonyloxy]phenyl 2 n-octyloxypropionate. The obtained composition showed an S$_C$* phase at −3° to 79° C. Thus an liquid crystal composition showing an S$_C$* phase over a wide temperature range involving room temperature was obtained.

EXAMPLE 49

The liquid crystal mixture comprising 23.65 of

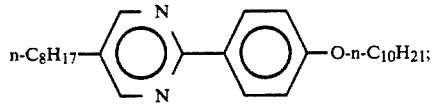

23.6% of

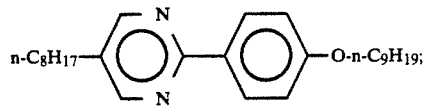

20.3% of

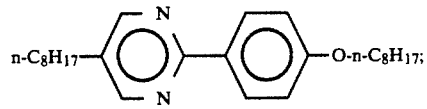

18.3% of

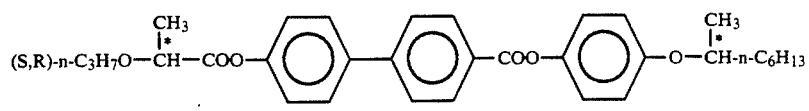

6.7% of

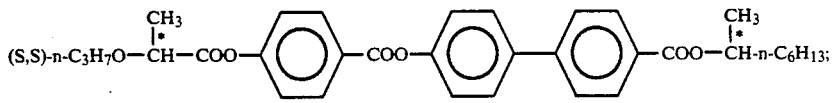

and 7.5% of the compound No. 29 in Table 1 showed an $S_C^*$ phase at 60° C. or below.

The electrooptical response speed of this liquid crystal mixture was determined in the same manner as described in Example 43. As a result, it showed a high speed response of 48 μsec at 25° C.

EXAMPLE 50

The compounds shown in Example 49 were mixed at a ratio of 23.5%, 23.5%, 20.2%, 12.3%, 3.7% and 16.8%, respectively. The liquid crystal mixture thus obtained showed an $S_C^*$ phase at 68° C. or below.

The electrooptical response speed of this liquid crystal mixture was determined in the same manner as described in Example 43. As a result, it showed a high speed response of 40 μsec at 25° C.

EXAMPLE 51

A chiral dopant comprising 73% of

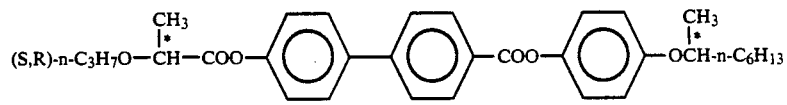

and 27% of

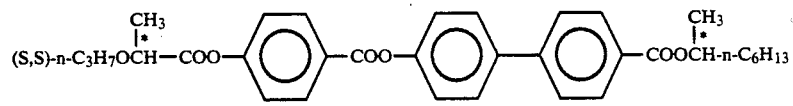

was prepared.

80% of the liquid crystal mixture showing an $S_C$ phase at 6° to 63.5° C. obtained in Example 42 was mixed with 20% of the above chiral dopant. The obtained liquid crystal composition showed an $S_C^*$ phase at 63° C. or below, an $S_A$ phase at 68° C. or below and an N* phase at 70° C. or below.

The electrooptical response of the liquid crystal mixture thus obtained was determined in the same manner as described in Example 43. As a result, it showed a high speed response of 39 μsec at 25° C.

The tilting angle thereof was 17°.

EXAMPLE 52

The procedure of Example 51 was repeated except that the compound No. 31 in Table 1 was replaced with the compound No. 32. The liquid crystal mixture thus obtained showed an $S_C^*$ phase at 63.5° C. or below, an $S_A$ phase at 68° C. or below and an N* phase at 71° C. or below.

The electrooptical response speed of this liquid crystal mixture was determined in the same manner as described in Example 43. As a result, it showed a high speed response of 46 μsec at 25° C.

The compound of the formula (I) of the present invention showed a smectic C phase a wide temperature range. When formulated into a composition showing a smectic C phase or a chiral smectic C phase, it can show a smectic C phase or a chiral smectic C phase over a wide temperature range.

As shown by the above Examples, the compound (I) can be readily prepared in an industrial manner. It is colorless per se and highly stable against light, moisture and heat. These properties make it highly useful in practice.

While the invention has been described in detail and with reference to specific embodiments thereof, it will be apparent to one skilled in the art that various changes and modifications can be made therein without departing from the spirit and scope thereof.

What is claimed is:

1. A compound represented by the following general formula:

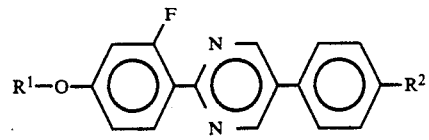

wherein $R^1$ and $R^2$ each independently represents a straight-chain or branched alkyl group containing 1 to 20 carbon atoms.

2. A compound as claimed in claim 1, wherein the branched moiety of said branched alkyl group is a methyl group.

3. A compound as claimed in claim 1, wherein $R^1$ and $R^2$ each independently represents a straight-chain alkyl group containing 1 to 20 carbon atoms.

4. A compound as claim in claim 1, wherein $R^1$ is a branched alkyl group containing 3 to 20 carbon atoms and $R^2$ is a straight-chain alkyl group containing 1 to 20 carbon atoms.

5. A compound as claimed in claim 4, wherein the branched moiety of said branched alkyl group is a methyl group.

* * * * *